(12) United States Patent
Wang

(10) Patent No.: US 6,485,751 B1
(45) Date of Patent: Nov. 26, 2002

(54) RESORBABLE CALCIUM PHOSPHATE-BASED BIO-COMPOUND PARTICLES AND THE MANUFACTURING PROCEDURE THEREOF

(75) Inventor: Yng-Jiin Wang, Taipei (TW)

(73) Assignee: Industrial Technology Research Institute, Hsinchu (TW)

( * ) Notice: Subject to any disclaimer, the term of this patent is extended or adjusted under 35 U.S.C. 154(b) by 0 days.

(21) Appl. No.: 09/583,992

(22) Filed: May 30, 2000

(51) Int. Cl.[7] ............................. A61K 9/50; A61K 9/14
(52) U.S. Cl. ...................... 424/499; 424/489; 424/491; 424/422; 424/423; 424/426; 424/602; 514/2
(58) Field of Search ................... 424/489, 491, 424/499, 422, 423, 426, 602; 514/2

(56) References Cited
U.S. PATENT DOCUMENTS 5,273,964 A * 12/1993 Lemons .................. 514/2
5,658,593 A * 8/1997 Orly et al. ............... 424/499

* cited by examiner

Primary Examiner—Thurman K. Page
Assistant Examiner—Liliana Di Nola-Baron
(74) Attorney, Agent, or Firm—W. Wayne Liauh

(57) ABSTRACT

This specification discloses resorbable calcium phosphate-based bio-compound particles and the manufacturing method thereof. Through the manufacturing process control, collagen has sufficient time to reconstruct and forms a network structure, which then combines with calcium phosphate-based ceramic powders that are controlled to have diameters $\leq 5$ μm so as to provide a bio-compound acceptable by humans and having a similar structure and constituents to the bony tissues. There is no need for a second operation when such material is used in medical practice and the bony tissues can undergo fast and effective bone-genesis.

17 Claims, 1 Drawing Sheet

RESORBABLE CALCIUM PHOSPHATE-BASED BIO-COMPOUND PARTICLES AND THE MANUFACTURING PROCEDURE THEREOF

BACKGROUND OF THE INVENTION

1. Field of Invention

The present invention relates to bio-compound particles and the manufacturing procedure thereof. More particularly, the present invention discloses a calcium phosphate-based bio-compound for use in bone operations and the method of manufacturing the same.

2. Related Art

Bone defects caused due to external forces or other diseases present major difficulties in orthopedic operations. Autogenous bone contains bone morphogenetic proteins and several live bone cells to facilitate recovery of bony tissues and thus become the best choice in bone transplantations. The autogenous bone graft material, however, is obtained from the patient in the operation, and it has the disadvantages that the patient could be infected after the operation and that the amount that can be obtained is very little. Allogenous bone graft, on the other hand, could result in problems such as virus infection (e.g., acquired immune deficiency) and imperfect recovery. Therefore, to facilitate the recovery of bone defects and to prevent the potential problems inherent in autogenous and allogenous transplantations, development in synthetic bone graft substitutes is necessary. The synthetic bone graft substitutes in the state of art cannot be dissolved or resorbed by human bodies, and have inferior properties in handling and moldability. Thus, it is urgent to develop resorbable bone graft substitutes with better handling and moldability to satisfy the needs of bone graft in cranio- and maxillo-facial surgeries, dental applications or orthopedic operations and bone-genesis.

The commercial product Collagraft of the prior art is a compound composed of bioceramics and collagen. However, the weight ratio between collagen and ceramics is very different from that for bony tissues. In spite of the fact that many researches indicate that Collagraft transplanted into animal bodies has good bone-genesis ability, the ceramics contains 60% of hydroxylapatite that cannot be resolved by living tissues.

The techniques disclosed in the U.S. Pat. Nos. 5,658,593 and 5,424,084 describe the methods for preparing such collagen microcapsules.

The network structure of the collagen is the main component of extracellular matrix; thus, collagen microcapsules with a network structure are more similar to living tissues. However, it is not clear from the known techniques disclosed in the patents whether the collagen microcapsules thus formed have a network structure. They also do not reveal any specific processes to form a network structure in the collagen microcapsules. Further, the percentage of collagen in known compounds of collagen and ceramics powders is far less than that in bony tissues.

SUMMARY OF THE INVENTION

In view of the foregoing, it is a primary object of the present invention to provide a family of resorbable calcium phosphate-based bio-compound particles, and the manufacturing procedure thereof, to solve problems in the current products in that the synthetic bone graft in the prior art cannot be resolved or absorbed by human bodies, has poor handling or moldability, and is inconvenient to use in clinic applications.

The present invention utilizes the dissolvable, osteo-conductive properties of collagen which can reconstitute into a network structures combines collagen with calcium phosphate-based ceramics powders, such as hydroxylapatite, so that calcium phosphate-based ceramics powders can homogeneously distribute within the reconstituted collagen network structure. In the microscopic structure of bony tissues, bio-apatite is nucleated on the network of osteo-conductive organic materials. In the present invention the compound formed by the calcium phosphate-based ceramics powders and the collagen network structure has a similar microscopic structure to the bony tissues.

Furthermore, the new bone-genesis filling materials prepared by the present invention use resorbable calcium phosphate-based compound particles, the weight ratio of collagen and ceramics powders reaching 35:65, which is similar to bony tissues. The diameters of the ceramics powders are no more than 5 $\mu$m; therefore, they can be absorbed by humans. Since the bone filling materials of the present invention have similar components and structures to bony tissues, there is no need for a second operation. They do not only have better handling and moldable properties, but also can fully utilize the re-genesis function of bony tissues to obtain fast and effective bone-genesis.

The resorbable calcium phosphate-based bio-compound prepared by the present invention can be used individually. Another object of the present invention is to, along with the self bone marrows of patients or applying the concept of tissue engineering, make the resorbable calcium phosphate-based bio-compounds prepared thereby the scaffolds of seeded cells and the carriers of relevant growth factors so as to fully utilize the re-genesis function of bony tissues for fast and effective bone-genesis around bone defects.

It is a further object of the present invention to provide a manufacturing technique for making the resorbable calcium phosphate-based bio-compound particles.

Pursuant the above objects, the manufacturing procedure for making the resorbable calcium phosphate-based bio-compound particles provided by the present invention comprises the steps of:

adding homogeneously mingled collagen and hydroxylapatite by droplets into an oil phase so that the collagen-hydroxylapatite mixture has enough time to reconstitute and form particles with a network structure, and obtaining the resorbable calcium phosphate-based bio-compound particle by cross-linking and isolation.

BRIEF DESCRIPTION OF THE DRAWINGS

The present invention will become more fully understood from the detailed description given hereinbelow illustration only, and thus are not limitative of the present invention, and wherein.

DETAILED DESCRIPTION OF THE INVENTION

Figure 1:
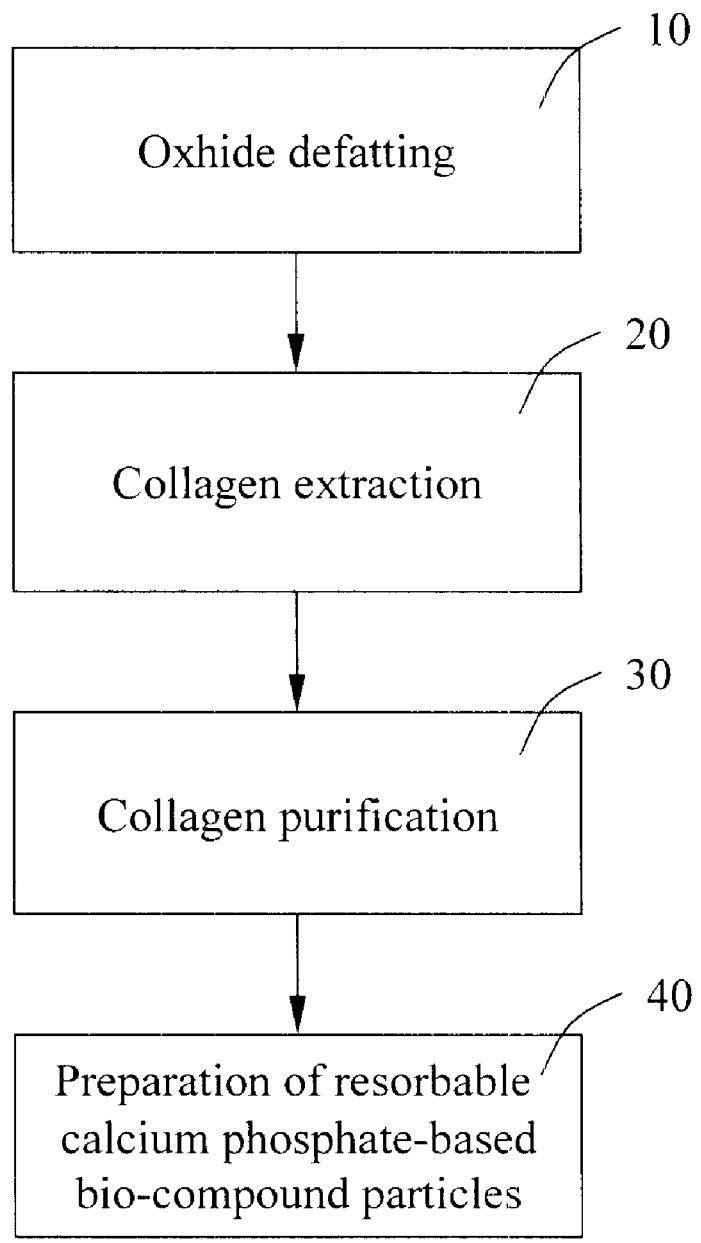
FIG. 1 is a flow diagram showing the manufacturing routine of resorbable calcium phosphate-based bio-compound particles according to the present invention.

The manufacturing procedure for making the resorbable calcium phosphate-based bio-compound particles provided by the present invention comprises the steps of: oxhide defatting, collagen extraction, collagen purification, and preparation of resorbable calcium phosphate-based bio-compound particles. Please refer to FIG. 1, which shows the flow of preparing the resorbable calcium phosphate-based bio-compound particles of the invention. The oxhide is first processed by defatting in step 10; collagen is extracted in step 20; the extracted collagen is further purified in step 30; and the resorbable calcium phosphate-based bio-compound particles are prepared in step 40.

The manufacturing procedure for making the resorbable calcium phosphate-based bio-compound particles of the invention is further described with a preferred embodiment hereinbelow. In the oxhide defatting step, an oxhide is obtained from a living being and kept in a refrigerator at −70° C. Hair stripping is performed with a razor at 4° C. and the oxhide is washed using a 4° C., 0.02M phosphate buffer solution (PBS). After being cut into chips with about 5 mm on each side, the oxhide chips are disposed into a solution with equal volumes of chloroform and methanol for defatting. The solution is replaced with new one when it becomes light yellow until the solution is transparent. The oxhide chips thus processed are put into 100% methanol to remove remaining chloroform. Finally, the oxhide chips is put into 50% methanol, and then into a solution of 0.15M sodium chloride and 50 mM TRIS buffer with pH=7.4.

In the collagen extraction step, the cleaned oxhide chips after defatting are placed in a 0.5M acetic acid solution. 0.5 mg/ml pepsin is added into the solution and the resulting solution is stirred homogeneously by a stir machine. After placing still for about 20 hours, the solution is processed by a high-speed centrifugal machine for collecting the upper layer of clean liquid. Sodium chloride is added into the clean liquid until its concentration is 2.5M and the whole solution is put still for about 20 hours. The high-speed centrifugal machine is used again to collect precipitate. The precipitate is mixed with TRIS buffer (pH=7.2–7.4) homogeneously and the resulting solution is placed still for about 20 hours. The resulting solution is centrifuged for collecting the upper layer of clean liquid. A solution of this clean liquid along with 1M sodium chloride and 50 mM TRIS buffer with pH=7.2–7.4 is performed with dialysis until the system is balanced at pH=7.2–7.4. Sodium chloride is added into the solution until its concentration reaches 1.8M. The resulting solution is stirred homogeneously by a stir machine and placed still for about 20 hours. The high-speed centrifugal machine is further used for collecting the upper layer of clean liquid. This clean liquid is again added with sodium chloride until the concentration of sodium chloride reaches 2.5M. This solution is subject to high-speed centrifugal force for collecting precipitate. The precipitate thus obtained is the Type I collagen. This precipitate is added with a proper amount of 0.5M acetic acid solution and stirred into homogeneity.

In the collagen purification step, the homogeneously stirred solution with the Type I collagen precipitate is poured into a dialytic bag. The 0.5M acetic acid solution is processed dialysis until the collagen in the dialytic bag becomes transparent. This collagen solution is preserved at −20° C.

In the step of preparing calcium phosphate-based bio-compound particles, the calcium phosphate-based ceramics powders that can be used in the present invention include hydroxylapatite, tricalcium phosphate, etc. Taking the preparing procedure of hydroxylapatite bio-compound particles as an example, the acidic collagen solution was dialyzed against 0.02 MPBS 9 phosphate buffered saline, pH (7.2–7.4), then 5 ml of collagen (6 mg/ml) is homogeneously mingled with 80 mg of hydroxylapatite at 4° C. The mingled solution is put into a syringe with a flat stainless needle and is pressured to for droplets by an injection pump. The droplets are dropped into 37° C. olive oil (or other non-biologically poisonous oils) and stirred for 1 hour using a stir machine so that the collagen-hydroxylapatite mixture has enough time to reconstitute into a network structure. The olive oil solution is gradually added with 2.5% of cross-linking agents by weight, which can be glutaraldehyde, genipin, or carbodiimide, so that the reconstituted collagen-hydroxylapatite particles cross-link in the presence of the cross-linking agents. The cross-linked particles have a dimension between 50 mm and 5 mm. The oil phase is sucked out and phosphate-based buffer solution is added therein to isolate remaining oil phase using a centrifugal machine. The cleaned collagen particles containing hydroxylapatite is cooled and dried and then preserved at −20°C.

EFFECT OF THE INVENTION

1. The calcium phosphate-based ceramics powders provided in the calcium phosphate-based bio-compound particles prepared by the present invention have diameters less than or equal to 5 $\mu$m. Compared with the previous U.S. Pat. Nos. 5,658,593 and 5,424,084, the present invention is resorbable and the collagen possesses reconstitutive properties so as to form a network structure similar to bony tissues. With such properties, minute calcium phosphate-based ceramics powders, such as hydroxylapatite, can be homogeneously distributed in the network structure of collagen.
2. Since the bone graft of the present invention has similar components and structure to bones tissues, there is no need for a second operation. It does not only have better handling and moldable properties, but also can fully utilize the re-genesis function of bones tissues to obtain fast and effect bone-genesis.
3. In addition to be singly applied, the resorbable calcium phosphate-based bio-compound prepared by the present invention can, along with the self bone marrows of patients or applying the concept of tissue engineering, be the scaffolds of seeded cells and the carriers of relevant growth factors so as to fully utilize the re-genesis function of bony tissues for fast and effective bone-genesis at bone defects.
4. The new bone graft prepared by the present invention uses resorbable calcium phosphate-based compound particles, the weight ratio of collagen and ceramics powders reaching 35:65, which is similar to bony tissues.
5. The weight ratio of the collagen and ceramics powders in the calcium phosphate base bio-compound particles of the invention can range from 10:90 to 100:0 according to different clinical needs.
6. The calcium phosphate base bio-compound particles of the invention can be immersed with medicines and hormone for curing osteoporosis and osteolysis, or with Chinese herbs for healing bone fractures.
7. The calcium phosphate base bio-compound particles prepared using the present invention can be applied in:
   orthopedics, dental applications, cranio- and maxillo-facial cosmetic surgeries;
   filling materials for bone fractures;
   scaffolds for tissue engineering products;
   spinal fusion;
   osteoporosis;
   as carriers for biological agents to, for example, encapsulate hormone or medicine for preventing osteoporosis, antibiotics for curing infection or inflammation, angio-genesis growth factors, bone-genesis growth factor, such as bone morphogenetic protein (BMPs), transformation growth factors (TGF-Beta), and Chinese herbs for healing orthopedic diseases.

The foregoing is a description of the arrangement and the operation of an embodiment of the present invention. The scope of the present invention is considered to include the described embodiment together with others obvious to those skilled in the art.

What is claimed is:

1. A manufacturing procedure for preparing resorbable calcium phosphate-based bio-compound particles, which comprises the steps of:

mingling collagen and calcium phosphate-based ceramics powders into a mixture solution;

adding the mixture solution by droplets into an oil phase in such a manner so as to cause the mixture solution to undergo reconstitution and form particles with a network structure;

adding a cross-linking agent to the oil phase for the particles to cross-link; and isolating the particles from the oil phase;

wherein the cross-linking agent is selected and process is conducted such that the particles prepared from the calcium phosphate-based ceramics powders have a dimension $\leq 5$ μm.

2. The manufacturing procedure of claim 1 further comprising the step of thoroughly stirring the mixture solution during the reconstituting process.

3. The manufacturing procedure of claim 1, wherein the particles are isolated from the oil phase through the steps of:

sucking the oil phase out of the mixture solution;

adding a buffer; and isolating the particles by centrifugally removing the remaining oil phase.

4. The manufacturing procedure of claim 3, wherein the buffer can be a phosphate-based buffer.

5. The manufacturing procedure of claim 1, wherein the step of adding the mixture solution by droplets to an oil phase is accomplished using a container with a needle.

6. The manufacturing procedure of claim 5, wherein the step of adding the mixture solution by droplets to an oil phase further comprises a step of squeezing the mixture solution into droplets with an injection pump.

7. The manufacturing procedure of claim 5, wherein the container can be a syringe.

8. The manufacturing procedure of claim 1, wherein the calcium phosphate-based ceramics powders in the mixture solution is hydroxylapatite.

9. The manufacturing procedure of claim 1, wherein the mingling is done at 4° C.

10. The manufacturing procedure of claim 1, wherein the calcium phosphate-based ceramics powder is tricalcium phosphate.

11. The manufacturing procedure of claim 1, wherein the oil phase can be olive oil or other non-biologically poisonous oil.

12. The manufacturing procedure of claim 1, wherein the cross-linking agent can be glutaraldehyde, genipin, or carbodiimide.

13. The manufacturing procedure of claim 1, wherein the calcium phosphate-based ceramics powders have dimensions $\leq 5$ μm.

14. The manufacturing procedure of claim 1, wherein the weight ratio between the ceramics powder and collagen ranges from 90:10 to 1:99.

15. A resorbable calcium phosphate-based bio-compound particle, comprising:

collagen with a network structure; and calcium phosphate-based ceramics powders with an average diameter $\leq 5$ μm homogeneously distributing in the network structure of collagen.

16. The resorbable calcium phosphate-based bio-compound particle of claim 15, wherein the calcium phosphate-based ceramics powder is hydroxylapatite.

17. The resorbable calcium phosphate-based bio-compound particle of claim 15, wherein the calcium phosphate-based ceramics powder is tricalcium phosphate.

* * * * *

UNITED STATES PATENT AND TRADEMARK OFFICE
CERTIFICATE OF CORRECTION

PATENT NO.      : 6,485,751 B1                                            Page 1 of 1
DATED           : November 26, 2002
INVENTOR(S)     : Yng-Jiin Wang, Fu-Yin Hsu and Shan-Chang Chueh It is certified that error appears in the above-identified patent and that said Letters Patent is hereby corrected as shown below:

<u>Title page,</u>
Item [75], please delete the Inventor information:
"Yng-Jiin Wang, Taipei (TW)", and substitute therefor
-- Yng-Jiin Wang, Fu-Yin Hsu, and Shan-Chang Chueh, all of Taipei (TW) --

Signed and Sealed this

Third Day of June, 2003

JAMES E. ROGAN
*Director of the United States Patent and Trademark Office*